US010315052B2

(12) United States Patent
Matubara et al.

(10) Patent No.: US 10,315,052 B2
(45) Date of Patent: Jun. 11, 2019

(54) PREDICTION DEVICE FOR SKIN CHANGE FROM RADIATION EXPOSURE, AND VERIFICATION DEVICE

(71) Applicant: National Institutes for Quantum and Radiological Science and Technology, Chiba-shi, Chiba (JP)

(72) Inventors: Hiroaki Matubara, Chiba (JP); Naruhiro Matufuji, Chiba (JP)

(73) Assignee: NATIONAL INSTITUTES FOR QUANTUM AND RADIOLOGICAL SCIENCE AND TECHNOLOGY, Chiba-shi (JP)

(*) Notice: Subject to any disclaimer, the term of this patent is extended or adjusted under 35 U.S.C. 154(b) by 242 days.

(21) Appl. No.: 15/129,749

(22) PCT Filed: Mar. 25, 2015

(86) PCT No.: PCT/JP2015/001692
§ 371 (c)(1),
(2) Date: Sep. 27, 2016

(87) PCT Pub. No.: WO2015/146164
PCT Pub. Date: Oct. 1, 2015

(65) Prior Publication Data
US 2017/0128748 A1    May 11, 2017

(30) Foreign Application Priority Data
Mar. 28, 2014   (JP) .................... 2014-068506

(51) Int. Cl.
*A61B 5/00*    (2006.01)
*A61N 5/10*    (2006.01)
*G06T 7/00*    (2017.01)
*G06T 7/90*    (2017.01)

(52) U.S. Cl.
CPC ............ *A61N 5/1071* (2013.01); *A61B 5/441* (2013.01); *G06T 7/0014* (2013.01); *G06T 7/90* (2017.01);
(Continued)

(58) Field of Classification Search
CPC ....... A61N 5/1071; G06T 7/90; G06T 7/0014; G06T 2207/10024; G06T 2207/30088; A61B 5/441
See application file for complete search history.

(56) References Cited

U.S. PATENT DOCUMENTS

| 2009/0003527 A1* | 1/2009 | Hoornaert | A61N 5/1048 378/97 |
| 2014/0094642 A1* | 4/2014 | Fuji | A61N 5/1031 600/1 |
| 2016/0136455 A1* | 5/2016 | Bharat | A61N 5/1039 600/1 |

FOREIGN PATENT DOCUMENTS

| JP | 10-244013 A | 9/1998 |
| JP | 2002-200050 A | 7/2002 |

(Continued)

OTHER PUBLICATIONS

International Search Report, dated Jun. 16, 2015, International Patent Application No. PCT/JP2015/001692 with English translation (4 pages).

*Primary Examiner* — Brenda C Bernardi
(74) *Attorney, Agent, or Firm* — Hamre, Schumann, Mueller & Larson, P.C.

(57) ABSTRACT

Provided is a prediction device for skin change from radiation exposure, the device being capable of precisely predicting a skin reaction to radiation exposure. Also provided are a verification device, a program for the prediction device for skin change, and a program for the verification device.

A prediction device (4) for skin change from radiation exposure includes: a radiation information accepting unit
(Continued)

(11) that accepts input of radiation information regarding expected exposure to radiation; a pre-exposure skin image acquiring unit (21) that acquires a skin image that captures skin of a living body; a change computing unit that computes the change of the skin due to exposure to the radiation determined by the radiation information and that obtains from the skin image a post-change prediction skin image; and a prediction skin image outputting unit (25) that outputs the prediction skin image. The change calculating unit includes an expression form converting unit (22), an amount-of-change deciding unit (13), an image changing unit (23), and an expression form restoring unit (24).

6 Claims, 7 Drawing Sheets

(52) U.S. Cl.
CPC ............... *G06T 2207/10024* (2013.01); *G06T 2207/30088* (2013.01)

(56) References Cited

FOREIGN PATENT DOCUMENTS

| | | | | |
|---|---|---|---|---|
| JP | 2009-523049 | A | 6/2009 | |
| JP | 2012-055510 | A | 3/2012 | |
| JP | 5274526 | B2 * | 8/2013 | ............... A61N 5/10 |
| WO | 2013-024534 | A1 | 8/2011 | |

* cited by examiner

PREDICTION DEVICE FOR SKIN CHANGE FROM RADIATION EXPOSURE, AND VERIFICATION DEVICE

TECHNICAL FIELD

The present invention relates to a prediction device for skin change and a prediction program for skin change for predicting skin change, for example, from radiation exposure beforehand. The present invention also relates to a verification device and a verification program for verifying a prediction result and actual skin change.

BACKGROUND ART

In radiation therapy, a living body such as a human or an animal is exposed to radiation from the outside of the living body, and tumors to be treated in the radiation therapy exist in the body in many cases. Thus, radiation therapy is always accompanied by a side effect, i.e. exposure of skin as a passage for radiation.

Skin after radiation therapy is irritated to turn red due to occurrence of an acute skin reaction in a radiation exposure region. Therefore, the radiation dose to tumors in radiation therapy is limited by the skin reaction. The skin reaction is also closely related to the quality of life (QOL) of a patient after therapy. Thus, if a skin reaction caused by radiation therapy can be predicted beforehand, the dose of exposure to radiation in the therapy can be easily decided, and the quality of life of a patient after therapy can be improved.

Here, examination of patent documents shows that a radiation monitor system for radiation therapy has been proposed (see Patent Document 1). The purpose of the system is to estimate the adsorbed dose of radiation applied to a patient undergoing radiation therapy.

However, the system is intended to measure the absorbed dose of exposure to radiation in practice, and is not intended to predict a skin reaction to radiation exposure beforehand.

PRIOR ART DOCUMENT

Patent Document

Patent Document 1: Japanese Translation of PCT Publication No. 2005-512028

SUMMARY OF THE INVENTION

Problems to be Solved by the Invention

In view of the problems described above, an object of the present invention is to provide a prediction device for skin change from radiation exposure, the device being capable of precisely predicting a skin reaction to radiation exposure beforehand; a verification device; a prediction program for skin change from radiation exposure; and a verification program.

Solutions to the Problems

The present invention provides a prediction device for skin change from radiation exposure, the device including: a radiation information accepting unit that accepts input of radiation information regarding expected exposure to radiation; a skin image acquiring unit that acquires a skin image that captures skin of a living body; a change computing unit that computes the change of the skin due to exposure to the radiation determined by the radiation information and that obtains from the skin image a post-change prediction skin image; and an outputting unit that outputs the prediction skin image. The present invention also provides a verification device using the prediction device for skin change from radiation exposure, a program for the prediction device for skin change from radiation exposure, and a program for the verification device.

Effects of the Invention

According to the present invention, there can be provided a prediction device for skin change from radiation exposure, the device being capable of precisely predicting a skin reaction to radiation exposure beforehand; a verification device; a prediction program for skin change from radiation exposure; and a verification program.

EMBODIMENTS OF THE INVENTION

Figure 1:
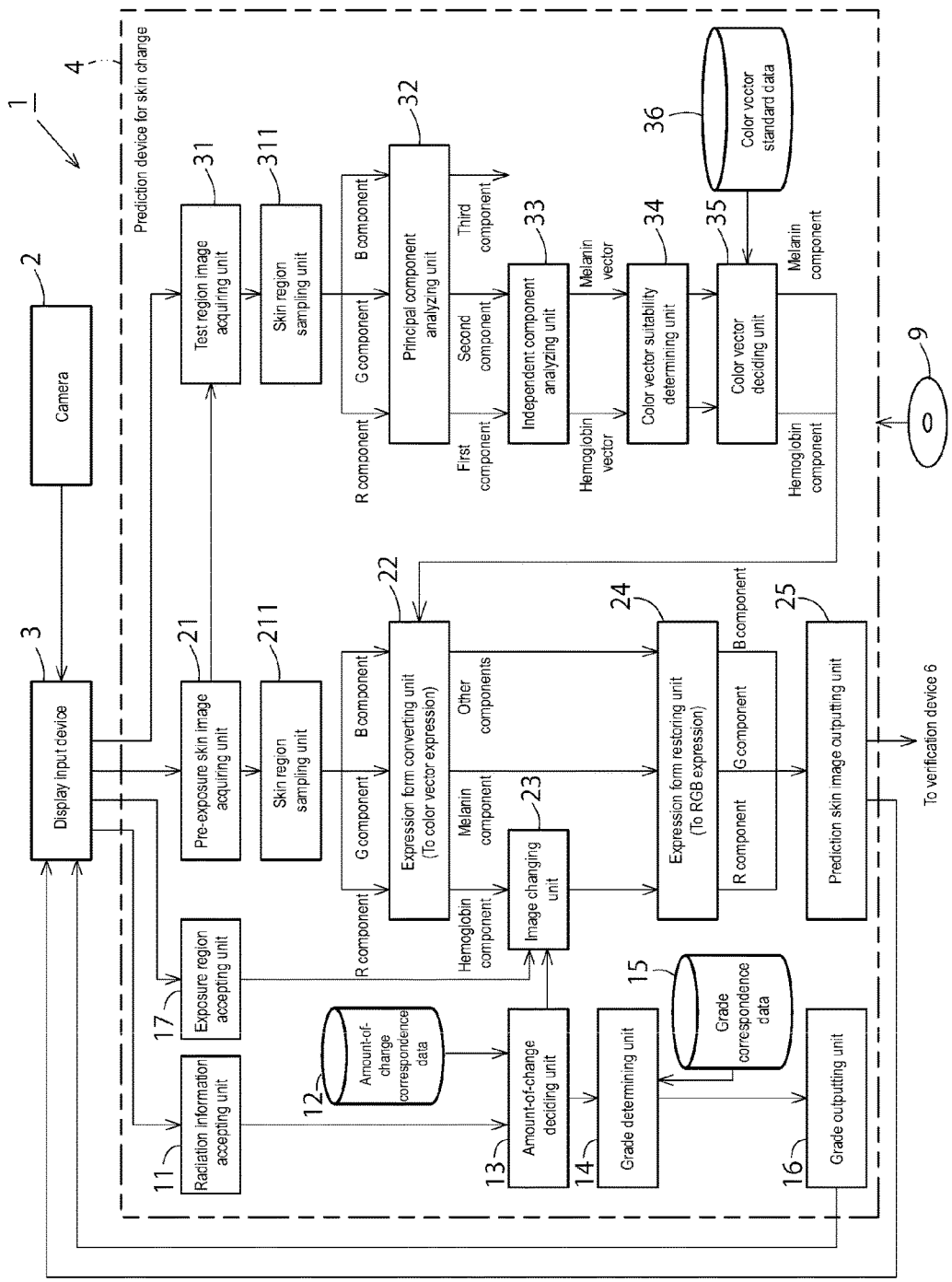
FIG. 1 is a block diagram showing a configuration of a prediction system for skin change.

In radiation therapies such as photon beam therapy and proton beam/heavy particle beam therapy, a skin reaction to radiation exposure is generally expressed in the following 4-stage grades.

Grade 1: light erythema
Grade 2: heavy erythema
Grade 3: blister, erosion
Grade 4: ulcer The grade expression is very rough, and currently, physicians visually observe the state of skin, and determine a grade. Thus, it is required to ensure that the grades can be quantitatively and precisely grasped, so that physicians can mutually communicate on a common scale.

The inventors studied a method capable of precisely predicting a skin reaction to radiation exposure before radiation therapy. At first, attention was given to turning of flesh to red due to the skin reaction, and an attempt was made to extract a R component (red component) from a RGB expression form image taken by a camera, followed by verifying a relationship between the dose of exposure of skin to radiation (hereinafter, referred to as a "skin dose") and the skin reaction, and preparing a skin image after radiation exposure.

However, when a test was actually conducted to examine a correlation between the skin dose in exposure and the degree of skin reaction obtained from the image that captured skin after exposure, the skin dose did not necessarily correspond to the amount of change of the R component. Thus, it was very difficult to precisely prepare a skin image after a skin reaction from radiation exposure by separating a component from a skin image that captured skin before radiation exposure.

The inventors extensively conducted studies, but a method for precisely predicting a skin reaction from a skin dose was not discovered until elapse of about 10 years after the studies were started.

Here, the reaction in which skin is irritated to turn red results from a biological reaction in which for restoring damaged cells, capillary blood vessels in the vicinity of the skin surface expand to increase the blood flow rate. Thus, the inventors gave attention to the possibility that the flow rate of hemoglobin as a pigment in blood correlates with the degree of skin reaction appearing as a red irritation. Attention was also given to the possibility that the hemoglobin flow rate also correlates with the dose of radiation required for therapy.

Then, if a correlation between the skin dose and the hemoglobin flow rate can be grasped from clinical data, it may be possible to quantitatively grasp a relationship between the skin dose and the skin reaction.

However, when only the hemoglobin flow rate is used as a scale, it is hard to have a sensible comprehension in communication among physicians, and it is desired to show the relationship with a visually recognizable skin reaction (light erythema, heavy erythema, blister/erosion and ulcer), particularly with a post-change skin image.

On the other hand, a technique for sampling from the RGB value of a digital image the relative pigment content of each of melanin and hemoglobin that are principal components constituting flesh color of the face for quantitatively evaluating the cosmetic effect and the health state has been developed (patent document: Japanese Patent Laid-open Publication No. 2002-200050; non-patent document: Tsumura N, et al.: Image-based skin color and texture analysis/synthesis by extracting hemoglobin and melanin information in the skin, ACM Trans. Graphics 22, 770, 2003.). When this technique is applied, a synthetic image with only the hemoglobin content intentionally manipulated from a photographed skin image can be obtained, and the manipulation can be selectively applied to only a specific region in the image.

However, skin reactions from radiation therapy include those of grade 1 (light erythema) to grade 4 (ulcer), and therefore cannot be expressed only by redness, and in past studies, a correlation between a change of the R component of a photographed image and a skin dose was not obtained. Therefore, it has been considered that application of the above-mentioned technique is difficult.

The inventors have extensively conducted studies, and resultantly conceived that importance may be given to grade 1 to grade 2 because radiation therapy is planned in grade 1 to grade 2. The inventors have then conceived the possibility that in grade 1 to grade 2, a correlation is obtained between the hemoglobin flow rate and the skin dose, and also a correlation is obtained between the hemoglobin flow rate and the skin reaction.

The inventors have then ensured that a skin image (reflected light) in the RGB expression form, which captures skin, is converted to a living body element expression form in which an image is expressed by living body elements (light absorption components) such as a hemoglobin component, the amount of change of the hemoglobin flow rate, which corresponds to a skin dose in expected exposure to radiation, is applied to the hemoglobin component among the living body elements, and the skin image is returned to the RGB expression form from the living body element expression form to successfully prepare a prediction skin image that shows a skin reaction corresponding to a skin dose.

The inventors have also achieved precise grade determination, and quantified and refined the scale in communication among physicians.

Hereinafter, one embodiment of the present invention will be described with reference to the drawings.

Examples

FIG. 1 is a block diagram showing a configuration of a skin change prediction system 1, FIGS. 2(A) to 2(D) are explanatory views of grade decision associated with radiation exposure, and FIGS. 3(A) to 3(E) are explanatory views of skin change.

As shown in FIG. 1, the skin change prediction system 1 includes a camera 2 that is a photographing device, a display input device 3 that is a personal computer, and a prediction device 4 for skin change that is a personal computer. The images in FIGS. 3(A) to 3(E) are originally color images, but all have a fixed and higher density as compared to actual images for clarification of a difference on the patent drawings that show monochromatic images.

Figure 3:
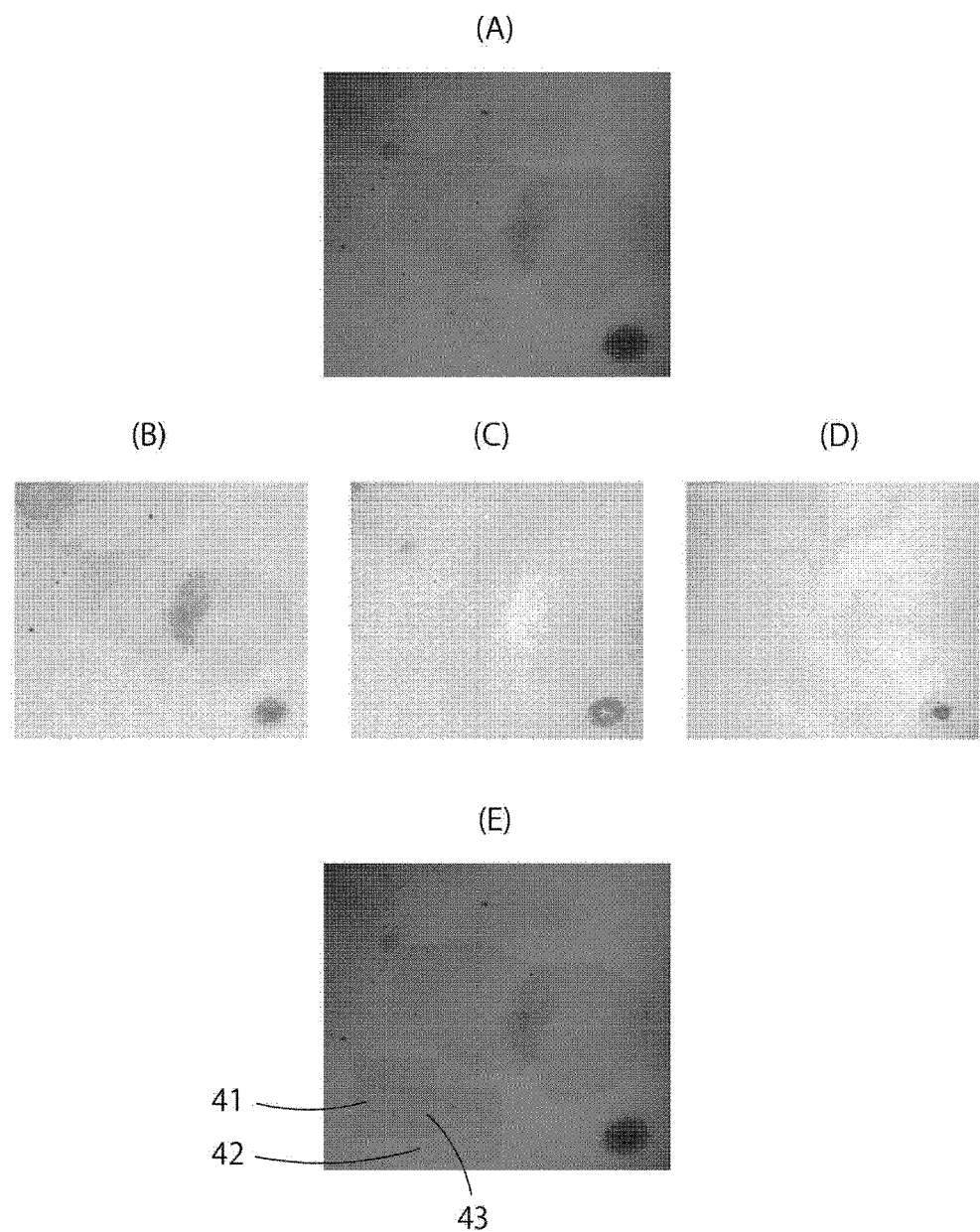
FIGS. 3(A) to 3(E) are explanatory views of skin change.

The camera 2 sends photographed image data (skin image color component data), which captures skin of a living body, to the display input device 3. The photographed image data is data of skin images in the RGB expression form as shown in FIG. 3(A) (the images are illustrated as monochromatic images, but are actually color images). The photographed image data acquired here requires a photographing environment in which the amount of illumination applied to skin to be photographed is uniform to a certain degree. The amount of illumination is not required to be strictly uniform as long as it is not unnaturally non-uniform.

The color components of a photographed image may include appropriate components that express colors, such as R component (red), G component (green) and B component (blue) that are the three primary colors of light (RGB expression form); or C component (cyan), M component (magenta) and Y component (yellow) that are the three primary colors (SMY expression form); or C component (cyan), M component (magenta), Y component (yellow) and K component (black) that are the four primary colors of printing (CMYK expression form). In this example, the three primary colors of light are used as preferred color components.

The display input device 3 includes an input unit such as a keyboard and mouse or a touch panel which accepts operation input; a display unit such as a liquid crystal display or a CRT monitor which displays an image; a storage unit such as a hard disk which stores data and programs; a control unit based on CPU, ROM and RAM, which performs various kinds of operations and computations in accordance with the programs; and a connection interface such as USB which is connected to external devices such as the camera 2 and the prediction device 4 for skin change, and sends and receives data.

The display input device 3 performs processing for sending photographed image data received from the camera 2 to the prediction device 4 for skin change; processing for displaying an input screen which includes a photographed image and an input section, and inputting a skin dose, an exposure region and a test region; and processing for sending the input skin dose, exposure region and test region to the prediction device 4 for skin change.

The prediction device 4 for skin change includes a storage unit which stores at least programs and data; a CPU which performs various kinds of operations and computations in accordance with the programs; and a connection interface such as USB which is connected to an external device such as the display input device 3. In the storage unit, a prediction program for skin change is installed from a recording medium 9. The prediction device 4 for skin change may further include an input unit, a display unit and so on as with the display input device 3. The prediction device 4 for skin change is also an image processing device that performs image processing.

The prediction device 4 for skin change includes a radiation information accepting unit 11 (factor information accepting unit), amount-of-change correspondence data 12, an amount-of-change deciding unit 13, a grade determining unit 14, grade correspondence data 15, a grade outputting unit 16, an exposure region accepting unit 17, a pre-exposure skin image acquiring unit 21 (skin image acquiring unit), a skin region sampling unit 211, an expression form converting unit 22, an image changing unit 23, an expression form restoring unit 24, a prediction skin image outputting unit 25, a test region image acquiring unit 31, a skin region sampling unit 311, a principal component analyzing unit 32, an independent component analyzing unit 33, a color vector suitability determining unit 34, a color vector deciding unit 35 and color vector standard data 36 as processing function units operated by the control unit in accordance with the programs in the storage unit. Among them, the expression form converting unit 22, the amount-of-change deciding unit 13, the image changing unit 23 and the expression form restoring unit 24 function as a change computing unit that computes skin change from radiation exposure.

The radiation information accepting unit 11 accepts input of radiation information (factor information) in a radiation therapy plan by the display input device 3. Acceptance of the radiation information may be performed by an appropriate method such as a method in which the information is manually input, or input from an information medium such as USB, or received through communication means from a therapy planning device. The radiation information accepted here is required to include at least a radiation type and a dose, and is required to further include radiation quality depending on a radiation type. Specifically, when the radiation type is an X ray, input of a dose is accepted. When the radiation type is a charged particle beam (protons, heavy ion particles including carbon), input of a dose and radiation quality is accepted. The dose is expressed as a physically measurable absorbed dose (unit: gray (Gy), or a clinical dose (unit: Gy(RBE) obtained by multiplying a biological effect ratio (RBE) as an index of a clinical effect, and the radiation quality is expressed as an added amount of energy per unit length of the particle (LET or linear energy, unit: keV/ micrometer). The radiation information also includes an elapsed time (the number of elapsed days) from a reference day as to timing of exposure to radiation. In this specification, the term "skin dose" refers to a dose regarding a X ray, and refers to a dose and radiation quality regarding a charged particle beam.

The amount-of-change correspondence data 12 is data in which the skin dose and the hemoglobin flow rate are made to correspond to each other. The data may be data in an appropriate form such as table data in which the values of the skin dose and the hemoglobin flow rate are made to correspond to each other, or calculation formula data such that the hemoglobin flow rate is calculated when the skin dose is input. The amount-of-change correspondence data 12 is prepared beforehand using clinical data, and registered, the clinical data being obtained in the following manner: the amount of hemoglobin in an exposure region is measured by a measurement device such as a laser blood flowmeter before and after skin dose exposure, and made to correspond to the skin dose.

The amount-of-change correspondence data 12 in this example will now be described in detail.

Figure 2:
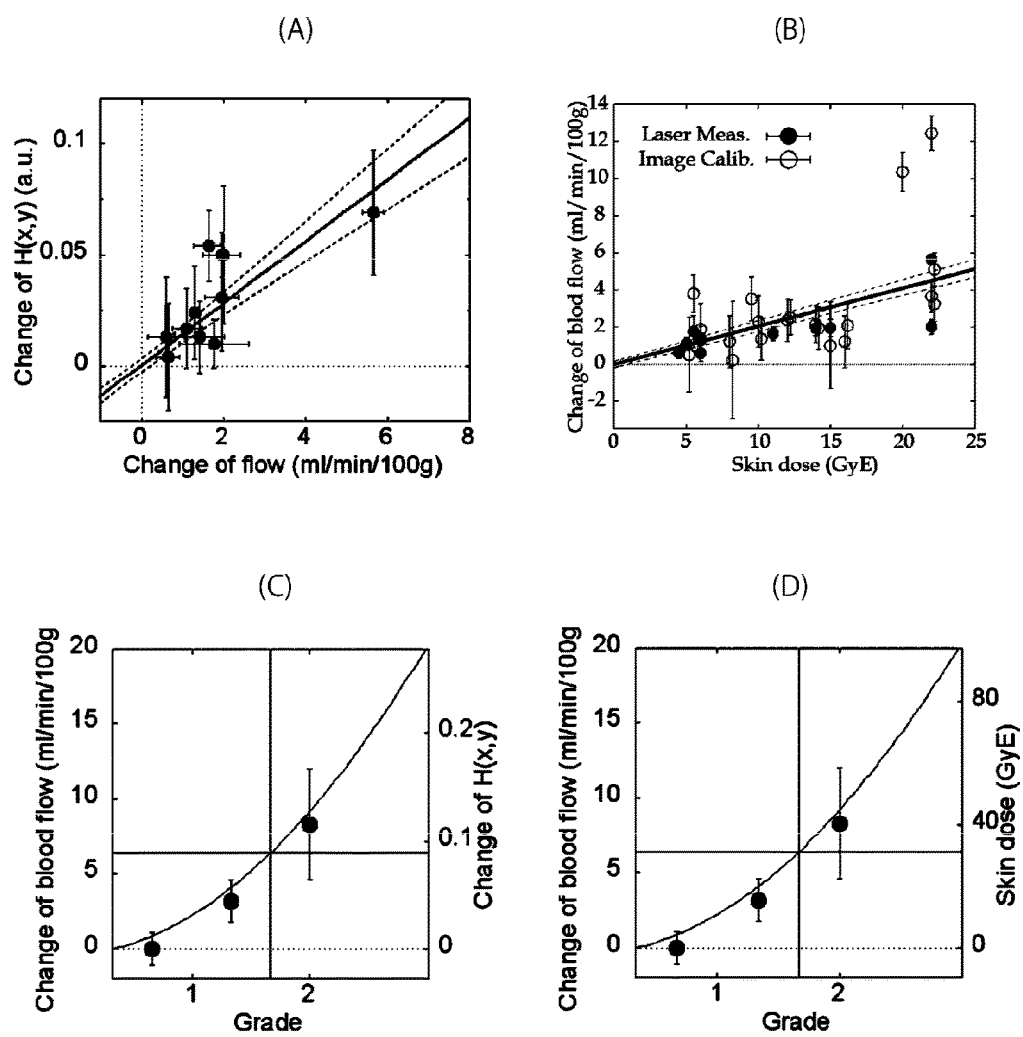
FIGS. 2(A) to 2(D) are explanatory views of grade decision associated with radiation exposure.

FIG. 2(A) is a graph obtained by plotting the results of measuring the amount of change of H(x,y) representing a pixel value of a hemoglobin pigment image and the amount of change of the hemoglobin flow rate (skin blood flow rate). When all data were fitted on a straight line passing through the origin, the gradient was 0.0139 (20) (ml/min 100 g)$^{-1}$. The correlation coefficient is 0.74, which indicates that there is a correlation between the amount of change of H(x,y) and the amount of change of the hemoglobin flow rate. The error band shown by dotted lines in the figure is calculated by squaring and summing an illumination environment-associated pixel value error of 15%, a blood flow rate measurement-associated error of 0.2 ml/min/100 g and a fitting-associated error. The blood flow rate measurement-associated error is principally caused by a biological effect from heart beats.

FIG. 2(B) is a graph obtained by plotting data regarding a relationship between the skin dose and the hemoglobin flow rate. This quantitative relationship is an important relationship to quantify the degree of erythema of skin in skin disorders. In the graph, the blackened symbols each represent data directly measured by a laser blood flowmeter, and the outlined symbols each represent a hemoglobin flow rate (blood flow rate) obtained by performing conversion from a pixel value resulting from image analysis by use of the relational formula in FIG. 2(A). As a result, a gradient of 0.205 (18) ml/min/100 g/Gy(RBE) was obtained. The correlation coefficient is 0.75 for only data by the laser, and 0.60 for all the data including images, and thus there is a correlation between the skin dose and the hemoglobin flow rate. Here, the error band shown by dotted lines in the figure is calculated by squaring and summing a blood flow rate measurement-associated error of 0.2 ml/min/100 g and a fitting-associated error.

Therefore, in this example, the gradient (0.0139 (20) (ml/min 100 g)$^{-1}$) of the amount of change of the hemoglobin flow rate (skin blood flow rate) with respect to the pixel value of the hemoglobin pigment image and the gradient (0.205 (18) ml/min/100 g/Gy (RBE)) of the skin dose with respect to the hemoglobin flow rate constitute the amount-of-change correspondence data 12.

Since as described above, there is a correlation between the pixel value of the hemoglobin pigment image and the hemoglobin flow rate (skin blood flow rate), and there is a correlation between the hemoglobin flow rate (skin blood flow rate) and the skin dose, the skin dose can be estimated from the amount of change of the pixel value in the hemoglobin pigment image, or inversely the amount of change of the pixel value in the hemoglobin pigment image can be estimated from the skin dose.

The amount-of-change deciding unit 13 decides the amount of change of the hemoglobin flow rate on the basis of radiation information acquired from the radiation information accepting unit 11, and the amount-of-change correspondence data 12. The decided amount of change is sent to the image changing unit 23.

The grade determining unit 14 determines a grade on the basis of radiation information received through the amount-of-change deciding unit 13 from the radiation information accepting unit 11, and the grade correspondence data 15. The grade determined here is a precise and detailed grade, for example, in 40-stage grades obtained by further enhancing the minuteness of the previous 4-stage grades by a factor of 10. The grade determining unit 14 sends the determined grade to the grade outputting unit 16.

The grade correspondence data 15 is data in which radiation information and a grade are made to correspond to each other, and the grade correspondence data 15 may be data in an appropriate form such as data in the form of a table, or a computation formula in which a radiation information value is substituted to obtain a solution.

The grade correspondence data 15 is prepared beforehand from clinical data. Specifically, FIG. 2(C) and FIG. 2(D) are graphs showing a relationship between grade determination and a hemoglobin flow rate (blood flow rate) that can be calculated from the amount of change of the pixel value, where the first ordinate (ordinate on the left in illustration) represents the hemoglobin flow rate (blood flow rate), and the abscissa represents the grade. The second ordinate (ordinate on the right in illustration) in FIG. 2(C) represents the amount of change of the pixel value, and the second ordinate (ordinate on the right in illustration) in FIG. 2(D) represents the skin dose.

From the graphs, it was specified in this example that the grade was 2 or higher when as the grade correspondence data 15, the hemoglobin flow rate (blood flow rate) increased by 6.4 ml/min/100 g or more. In this example, the amount of change of the pixel value and the skin dose, which correspond to the boundary line of grade ½, can be calculated by using a conversion coefficient with the change of the hemoglobin flow rate (change of the blood flow rate), and the amount of change of the pixel value and the skin dose are supposed to be 0.09 and 32 Gy(RBE), respectively. The error in this case is ±20%.

The threshold value in grade determination is not limited to the above-described value, and can be appropriately defined. What is important is that as shown in the graphs, the hemoglobin flow rate (blood flow rate), the skin dose and the amount of change of the pixel value each quantitatively correspond to a precise grade value on a one-to-one basis.

The grade outputting unit 16 sends to the display input device 3 a grade obtained in the grade determining unit 14, and displays the grade on the display input device 3 as a grade display screen. The exposure region accepting unit 17 accepts, from the display input device 3, input of an exposure region of skin of a living body which is exposed to radiation in a radiation therapy plan. The exposure region accepting unit 17 sends the accepted exposure region to the image changing unit 23.

The pre-exposure skin image acquiring unit 21 acquires pre-exposure skin image data, which captures skin before radiation exposure, from the display input device 3. The pre-exposure skin image data is in the RGB expression form, and therefore can be easily separated into a R component, a G component and a B component. The pre-exposure skin image acquiring unit 21 sends the separable pre-exposure skin image data to the expression form converting unit 22.

The skin region sampling unit 211 samples a skin region (flesh region) from the pre-exposure skin image data acquired in the pre-exposure skin image acquiring unit 21. Sampling of the skin region is performed by sampling pixels satisfying skin region conditions among the pixels of the pre-exposure skin image data.

For the skin region conditions, pixels satisfying all of the following conditions in the RGB expression form are defined as a skin region.

<Skin Region Conditions>
$R > R\_th$
$G/R > R\_ratio1$
$B/R > R\_ratio2$ (Note) R represents the density of the R component (e.g. 0 to 255).

G represents the density of the G component (e.g. 0 to 255).

B represents the density of the B component (e.g. 0 to 255).

R_th is a predetermined value, and can be set to, for example, 100 to 160, or 10. R_th can be set to 10 or more, and is preferably 50 or more, more preferably 100 or more. R_th is preferably 200 or less, more preferably 160 or less.

R_ratio1 is a predetermined value, and can be set to an appropriate value such as, for example, 1.1 or 1.0. R_ratio1 is preferably 0.5 to 1.5, more preferably 0.9 to 1.2, further preferably 1.0 to 1.1.

R_ratio2 is a predetermined value, and can be set to an appropriate value such as, for example, 1.1 or 1.0. R_ratio2 is preferably 0.5 to 1.5, more preferably 0.9 to 1.2, further preferably 1.0 to 1.1.

Photographing conditions for obtaining a suitable image under the conditions for sampling a skin region include only the following two conditions: (1) a sufficient brightness is kept to ensure that the flesh color can be recognized; and (2) a skin region is illuminated without generation of an unnatural shadow and halation. As long as these two conditions are satisfied, the sampling of a skin region is satisfactorily performed. In the condition (2), it is preferable that the skin region is substantially uniformly illuminated.

The expression form converting unit 22 converts the acquired pre-exposure skin image data (skin region sampling completed) from the RGB expression form to a color vector expression form. The conversion is performed by using a color vector received from the color vector deciding unit 35. Here, the color vector refers to a hemoglobin vector and a melanin vector in this embodiment. In the color vector expression form, information is separated into three components: a hemoglobin component, a melanin component and other components. Details of changing of the expression form by the expression form converting unit 22 will be described later.

The image changing unit 23 applies the amount of change, which is decided by the amount-of-change deciding unit 13, to an exposure region specified by the exposure region accepting unit 17 in a hemoglobin component sampled from pre-exposure skin image data by the expression form converting unit 22, so that the hemoglobin component of the exposure region is changed. Details of image changing processing by the image changing unit 23 will be described later.

The expression form restoring unit 24 performs restoration of the expression form by converting to the RGB expression form the image data in the color vector expression form (skin image living body element component data) after the image data is changed by the amount-of-change deciding unit 13. The expression form restoring unit 24 sends the image data in the RGB expression form after restoration to the prediction skin image outputting unit 25 as prediction skin image.

The prediction skin image outputting unit 25 sends the received prediction skin image to the display input device 3 to display the prediction skin image.

The test region image acquiring unit 31 acquires a test region input by the display input device 3. The test region is a region selected as a part of the photographed skin image, and may be an appropriate region such as, for example, a small region of 100 pixels×100 pixels.

The skin region sampling unit 311 samples a flesh image by performing the same operation as with the skin region sampling unit 211 for the skin image of the test region. A configuration may be employed in which the skin region sampling unit 311 is not provided, and the test region image acquiring unit 31 samples a test region from the skin region sampled by the skin region sampling unit 211.

The principal component analyzing unit 32 performs principal component analysis (a type of multi-variable analysis) for the skin image of the test region (skin region sampling completed). The principal component analyzing unit 32 extracts a coordinate axis of a principal component (first axis of the first component) in a direction with the highest correlation (direction with the broadest distribution), and subsequently repeats the operation of extracting the nth axis of the nth component in a direction with the highest correlation (direction with the broadest distribution) on a plane (plane on multi-dimensions) orthogonal to the previous coordinate axes. The result of computation shows that 98% or more of the skin image can be expressed by two axes: the first component (first axis) with the highest correlation and the second component (second axis) orthogonal to the first component. Thus, the other components are discarded collectively as a third component, and in subsequent processing, only the first component and the second component are used. Accordingly, the prediction device 4 for skin change achieves precise and quick processing. Expression with vectors obtained by subjecting image data in the test region image to principal component analysis gives the following formula shown in (Formula 1).

$$\begin{pmatrix} r_{test} \\ g_{test} \\ b_{test} \end{pmatrix} = \begin{pmatrix} r_0 \\ g_0 \\ b_0 \end{pmatrix} + \begin{pmatrix} r_{ave} \\ g_{ave} \\ b_{ave} \end{pmatrix} + pc1 \begin{pmatrix} r_1 \\ g_1 \\ b_1 \end{pmatrix} + pc2 \begin{pmatrix} r_2 \\ g_2 \\ b_2 \end{pmatrix} + pc3 \begin{pmatrix} r_3 \\ g_3 \\ b_3 \end{pmatrix} \quad \text{[Formula 1]}$$

(Note) $(r_0, g_0, b_0)$ represents a flesh base color.

$r_{ave}$, $g_{ave}$ and $b_{ave}$ represent averages of values after subtracting the values of $(r_0, g_0, b_0)$ from the values of $(r, g, b)$, respectively, in the image.

pc1 represents the first component, pc2 represents the second component, and pc3 represents the third component.

$(r_1, g_1, b_1)$ represents a vector expressing the first component.

$(r_2, g_2, b_2)$ represents a vector expressing the second component.

$(r_3, g_3, b_3)$ represents a vector expressing the third component.

The vectors are normalized to 1, and are mutually orthogonal, and therefore the inner product of the vectors is 0.

The independent component analyzing unit 33 performs independent component analysis (a type of multi-variable analysis) for the data expressed by the first component and the second component obtained in the principal component analyzing unit 32, and takes two non-orthogonal coordinate axes with each axis being in the most independent state. One of the components of the obtained coordinate axes is a hemoglobin vector, and the other component is a melanin vector. Expression with vectors obtained by subjecting image data in the test region image to independent component analysis gives the following formula shown in (Formula 2).

$$\begin{pmatrix} r_{test} \\ g_{test} \\ b_{test} \end{pmatrix} \cong \begin{pmatrix} r_0 \\ g_0 \\ b_0 \end{pmatrix} + \begin{pmatrix} r_{ave} \\ g_{ave} \\ b_{ave} \end{pmatrix} + h \begin{pmatrix} r_h \\ g_h \\ b_h \end{pmatrix} + m \begin{pmatrix} r_m \\ g_m \\ b_m \end{pmatrix} \quad \text{[Formula 2]}$$

(Note) $r_{ave}$, $g_{ave}$ and $b_{ave}$ represent averages of values after subtracting the values of $(r_0, g_0, b_0)$ from the values of $(r, g, b)$, respectively, in the image.

$(r_h, g_h, b_h)$ represents a hemoglobin vector.

$(r_m, g_m, b_m)$ represents a melanin vector.

h represents a coefficient showing a hemoglobin amount (hemoglobin coordinate).

m represents a coefficient showing a melanin amount (melanin coordinate).

The reason why an approximate equal sign is used rather than an equal sign is that the third component is excluded. The color vectors are normalized to 1, but the color vectors are not mutually orthogonal.

The above (Formula 1) and (Formula 2) clearly show that the averages $r_{ave}$, $g_{ave}$ and $b_{ave}$ are added to the components, but the averages $r_{ave}$, $g_{ave}$ and $b_{ave}$ may be included in $R_0$, $B_0$ and $G_0$, respectively, in the formulae: (Formula 1) and (Formula 2), and made apparently invisible. In this case, a formula having the same meaning is obtained, and therefore the RGB expression form can be converted to a living body element expression form using a hemoglobin vector etc.

The color vector suitability determining unit 34 determines whether the obtained color vector is suitable or not. Specifically, the test region acquired in the test region image acquiring unit 31 must ensure that hemoglobin and melanin are selected as the first component and the second component in the principal component analyzing unit 32, and separated as independent components in the independent component analyzing unit 33. For determining whether or not such a test region has been input in the display input device 3 by an operator, the color vector suitability determining unit 34 determines whether or not the obtained color vectors are a hemoglobin vector and a melanin vector.

If the determination result from the color vector suitability determining unit 34 shows "suitable", the color vector deciding unit 35 decides as color vectors the hemoglobin vector and the melanin vector sent from the independent component analyzing unit 33. If the determination result from the color vector suitability determining unit 34 shows "not suitable", the color vector deciding unit 35 acquires a standard hemoglobin vector and melanin vector from the color vector standard data 36, and decides these vectors as color vectors. The color vector deciding unit 35 sends the decided hemoglobin vector and melanin vector to the expression form converting unit 22. In this example, the color vector standard data 36 is used if it is once determined that the color vectors are not suitable, but the present invention is not limited thereto, and a configuration may be employed in which the operations ranging from acquirement of a test region to determination of suitability are repeated multiple times, and if all the results show "not suitable" when the operations are repeated a predetermined number of times, the color vector standard data 36 is used.

The color vector standard data 36 stores standard color vectors (hemoglobin vector and melanin vector) calculated beforehand.

<Details of Changing of Expression Form by Expression Form Converting Unit 22>

The expression form converting unit 22 linearly converts (coordinate-converts) the three components of (r, g, b) to the three components of (h, m, s) shown in the following formula (Formula 3) using the color vectors obtained by the independent component analyzing unit 33.

$$\begin{pmatrix} r \\ g \\ b \end{pmatrix} = \begin{pmatrix} r_0 \\ g_0 \\ b_0 \end{pmatrix} + h \begin{pmatrix} r_h \\ g_h \\ b_h \end{pmatrix} + m \begin{pmatrix} r_m \\ g_m \\ b_m \end{pmatrix} + s \begin{pmatrix} 1/\sqrt{3} \\ 1/\sqrt{3} \\ 1/\sqrt{3} \end{pmatrix} \quad \text{[Formula 3]}$$

(Note) s is a coefficient of the unit vector of illumination (shade vector), and corresponds to one including all information unable to be expressed by color vectors of hemoglobin and melanin.

Linear conversion to (Formula 3) will now be described. For more correctly expressing (Formula 3), the following (Formula 4) can be given.

$$\begin{pmatrix} r(x,y) \\ g(x,y) \\ b(x,y) \end{pmatrix} = \begin{pmatrix} r_0 \\ g_0 \\ b_0 \end{pmatrix} + H(x,y) \begin{pmatrix} r_h \\ g_h \\ b_h \end{pmatrix} + M(x,y) \begin{pmatrix} r_m \\ g_m \\ b_m \end{pmatrix} + S(x,y) \begin{pmatrix} 1/\sqrt{3} \\ 1/\sqrt{3} \\ 1/\sqrt{3} \end{pmatrix} \quad \text{[Formula 4]}$$

(Note) Variables that are two-dimensional position functions of (x, y) take different values for each pixel of image data.

A part that is not in the form of functions of (x, y) means a constant.

The (Formula 4) shows that the full-color image expressed by (r(x, y), g(x, y), b(x, y)) is resolved into three pigment images of (H(x, y), M(x, y), S(x, y)).

Here, H(x, y), M(x, y) and S(x, y) can be expressed by the following (Formula 5).

$$H(x,y) = h(x,y) + h_{ave}$$

$$M(x,y) = m(x,y) + m_{ave}$$

$$S(x,y) = s(x,y) + s_{ave} \quad \text{[Formula 5]}$$

(Note) $h_{ave}$, $m_{ave}$ and $S_{ave}$ represent averages for the components of h, m and s, respectively. The averages each may be an appropriate average such as an average over the whole image, but it is preferably an average calculated from each of the RGB components of only a region expressing skin. Therefore, in this example, an average for each of the RGB components of the skin region is used.

h(x, y), m(x, y) and s(x, y) in the (Formula 5) are derived from the following calculation formula of (Formula 6) using the principal component vectors of the first component and the second component obtained by performing principal component analysis shown in the (Formula 1).

$$h(x,y) = \frac{(r(x,y)-g(x,y))*(r2-b2)-(r(x,y)-b(x,y))*(r2-g2)}{(r1-b1)*(r2-b2)-(r1-b1)*(r2-g2)}$$

$$m(x,y) = \frac{(r(x,y)-g(x,y))*(r1-b1)-(r(x,y)-b(x,y))*(r1-g1)}{(r1-b1)*(r2-g2)-(r1-g1)*(r2-b2)}$$

[Formula 6]

$$u(x,y) = \frac{\sqrt{3}}{(g2-r2)} \left\{ \begin{array}{l} (r(x,y)*g2 - g(x,y)*r2) - \\ (r1*g2 - g1*r2)*h(x,y) \end{array} \right\}$$

$h_{ave}$, $m_{ave}$ and $s_{ave}$ can be derived from a formula in which the parts of r(x, y), g(x, y), b(x, y) and h(x,y) in the (Formula 6) are replaced by $r_{ave}$, $g_{ave}$, $b_{ave}$ and $h_{ave}$, respectively.

By the conversion of the expression form, the skin image shown in FIG. 3(A) is separated into a hemoglobin component skin image shown in FIG. 3(B), a melanin component skin image shown in FIG. 3(C) and the other components skin image shown in FIG. 3(D). These figures show monochromatic images, but actually, the image in FIG. 3(B) is a single-color scale image of pale red, the image in FIG. 3(C) is a single-color scale image of pale ocher, and the image in FIG. 3(D) is a single-color scale image of pale gray (grayscale image). For example, a blue blood vessel cannot be expressed by a color vector of hemoglobin or melanin, and thus makes its appearance in the form of a shadow in FIG. 3(D) that is associated with the other components. Examples shown in FIGS. 3(B) to 3(D) are images when the expression form is converted without performing skin region sampling, and for example, in the case of an image that captures a matter other than skin, such as a background, a more satisfactory hemoglobin component skin image is obtained when skin region sampling is performed for the averages $r_{ave}$, $g_{ave}$ and $b_{ave}$ (see FIGS. 7(A) to 7(D) described later).

In this example, pigment components: a hemoglobin component and a melanin component are used as living body element components, but the present invention is not limited thereto, and a configuration may be employed in which other components are used. In this case, a hemoglobin component, a eumelanin component, a phaeomelanin component, a carotene component or two or more thereof can be used, and among them, a eumelanin component and a phaeomelanin component can be considered collectively as a melanin component. It is preferable that living body element components include at least a hemoglobin component irrespective of which configuration is employed.

<Details of Image Changing Processing by Image Changing Unit 23>

The image changing unit 23 adds the amount of change (hemoglobin increase amount), which is decided in the amount-of-change deciding unit 13, to the h component in the (Formula 3).

When the image is changed in this way and then the components are combined to restore the image to the original RGB expression form, a prediction skin image shown in FIG. 3(E) is obtained. The prediction skin image in FIG. 3(E) is a monochromatic image for a patent drawing, but is actually a color image. The example in FIG. 3(E) shows a prediction skin image when a tetragonal first exposure region 41, and a tetragonal second exposure region 42 which partially overlaps the first exposure region 41 are each exposed to radiation. The first exposure region 41 and the second exposure region 42 are the regions accepted in the exposure region accepting unit 17. The first exposure region 41 has a larger skin dose than the second exposure region 42, and is therefore displayed more deeply (in red) than the second exposure region 42, and a overlapped exposure region 43 where the first exposure region 41 and the second exposure region 42 overlap each other is displayed still more deeply (in red).

The display input device 3 and the prediction device 4 for skin change are configured as different devices, but may be collectively configured as one device. In this case, the devices can be configured as one computer. For example, a display input unit such as a touch panel monitor, or an input unit such as a keyboard and mouse, and a display unit such as a liquid crystal display or a CRT monitor can be integrated as the display input device 3. For example, a control unit and a storage unit can be integrated as the prediction device 4 for skin change. Accordingly, the display input device 3 and the prediction device 4 for skin change can be configured in one computer.

Figure 4:
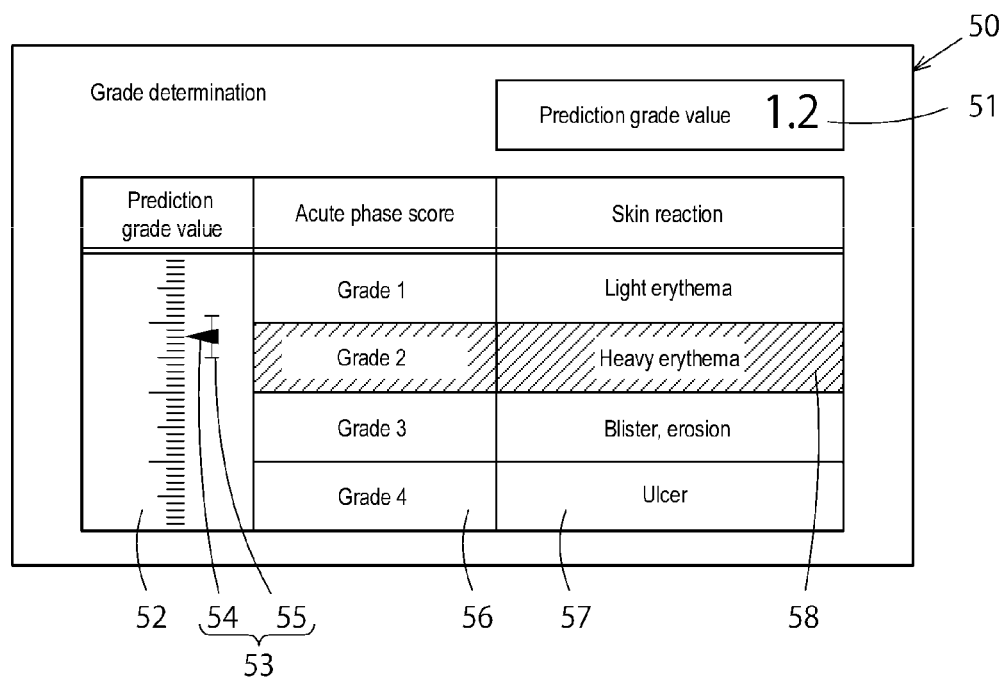
FIG. 4 is a screen block diagram of a grade determination screen.

FIG. 4 is a screen block diagram of a grade determination screen 50 that displays a grade output to the display input device 3 by the grade outputting unit 16.

The grade determining screen 50 includes a prediction grade value display section 51, a prediction grade scale display section 52, an acute phase score display section 56 and a skin reaction display section 58.

The prediction grade value display section 51 displays a grade value determined by the grade determining unit 14. The grade value is a value which can be shown in more minute stages as compared to the previous 4 stages (grades 1 to 4), and is displayed in, for example, 40 stages (grades 0.1 to 4.0).

It is preferable to specify which grade values in these minute stages correspond to each of the previous 4-stage grades, and in this example, grades 0.1 to 1.0 in the grades according to the present invention (hereinafter, referred to as new grades) correspond to grade 1 in the previous grades, grades 1.1 to 2.0 in the new grades correspond to grade 2 in the previous grades, grades 2.1 to 3.0 in the new grades correspond to grade 3 in the previous grades, and grades 3.1 to 4.0 in the new grades correspond to grade 4 in the previous grades.

The prediction grade scale display section 52 shows scales in which the previous grades are minutely divided corresponding to the new grades, and displays a prediction value mark 53 that points the scale.

The prediction value mark 53 includes a prediction value indicating section 54 that correctly indicates a prediction value; and an error range display section 55 that indicates a range in which an error may occur from the prediction value. The error range display section 55 has a width in a report in which scales of the prediction grade scale display section 52 are arranged, and the prediction value mark 53 is provided so as to overlap inside the error range display section 55, so that the median and the error range of the prediction value can be intuitively and intelligibly recognized. The error displayed in the error range display section 55 can be determined by an appropriate method, such as a method in which the error is set in a certain range determined beforehand, or the error is determined by computation each time. When the error is set in a certain range determined beforehand, for example an error (e.g. 18% to 21%) with a photographing environment-dependent error (e.g. 15%) added to an error (e.g. 10% to 15%) of the hemoglobin amount measured by a laser blood flowmeter can be displayed.

The acute phase score display section 56 shows previous grades 1 to 4, and the skin reaction display section 58 displays "light erythema", "heavy erythema", "blister, erosion" and "ulcer" that are skin reactions corresponding to previous grades 1 to 4, respectively, in correspondence to respective grades.

The acute phase score display section 56 and the skin reaction display section 58 performs differentiation display 58 in which a grade part where a predicted new grade is positioned is displayed in color. Accordingly, which grade in the previous grades corresponds to the new grade can be easily known.

Figure 5:
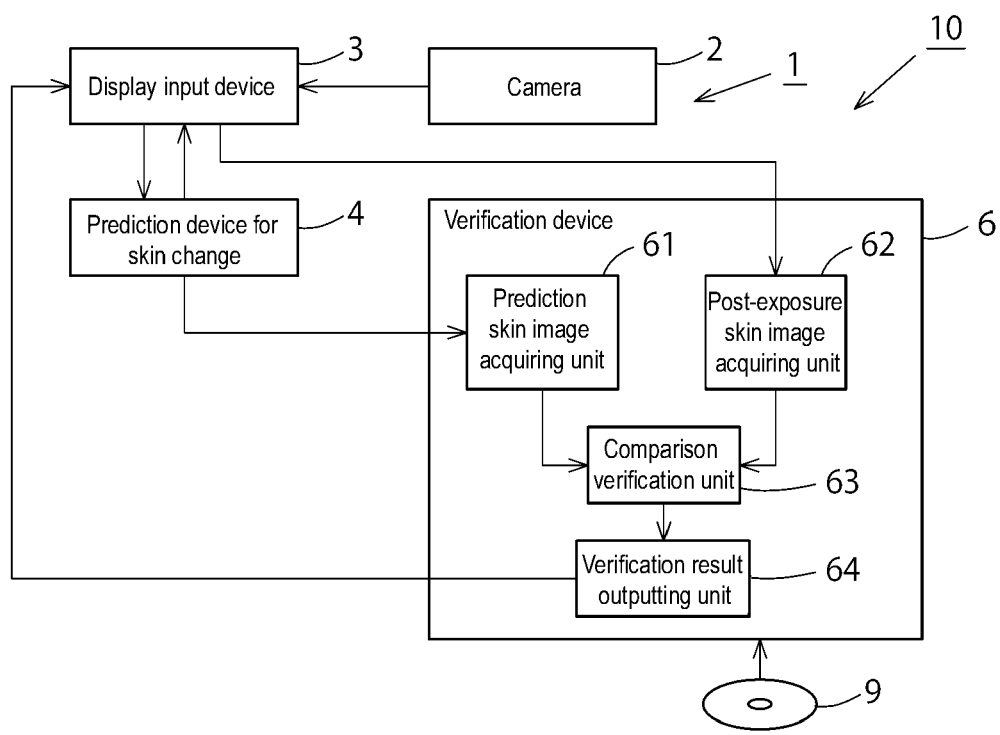
FIG. 5 is a block diagram showing a configuration of a verification system for skin change.

FIG. 5 is a block diagram showing a configuration of a verification system 10 for skin change with a verification device 6 added to the prediction system 1 for skin change which has been so far described.

The verification device 6 includes a prediction skin image acquiring unit 61, a post-exposure skin image acquiring unit 62, a comparison verification unit 63 and a verification result outputting unit 64. The verification device 6 includes a storage unit which stores at least programs and data; a CPU which performs various kinds of operations and computations in accordance with the programs; and a connection interface such as USB which is connected to an external device such as the prediction device 4 for skin change. In the storage unit of the verification device 6, a verification program is installed from the recording medium 9. The verification device 6 may be hardware different from that of the prediction device 4 for skin change, or may be configured with a function incorporated in the same hardware as in the prediction device 4 for skin change.

The prediction skin image acquiring unit 61 acquires a prediction skin image from the prediction skin image outputting unit 25 of the prediction device 4 for skin change (see FIG. 1).

The post-exposure skin image acquiring unit 62 acquires a post-exposure skin image, which captures skin photographed by the camera 2 after radiation exposure, through the display input unit 3.

The comparison verification unit 63 compares the prediction skin image received from the prediction skin image acquiring unit 61 and the post-exposure skin image received from the post-exposure skin image acquiring unit 62, and verifies suitability of an exposure region and skin change for a radiation exposure plan. Specifically, a degree of coincidence between a region where a skin reaction occurs due to radiation exposure and an exposure region in a radiation exposure plan is calculated, and suitability is determined in accordance with whether or not the degree of coincidence falls within a predetermined range. Here, the prediction skin image received from the prediction skin image acquiring unit 61 is an image predicted on the basis of, for example, radiation information planned in a separate therapy planning device. Therefore, radiation information regarding the therapy plan may be absent at this time, or radiation information may be obtained to perform comparison verification more in detail.

A degree of coincidence between the degree at which skin undergoing a skin reaction is different in color from surrounding skin and the degree at which the color is changed through a radiation therapy plan is calculated, and suitability is determined in accordance with whether or not the degree of coincidence falls within a predetermined range. The calculation of the degree of coincidence regarding color change can be performed by an appropriate method such as a method in which the prediction skin image is directly compared with the post-exposure skin image, or the expression form is converted to color vector expression by the expression form converting unit 22, and only hemoglobin components are compared.

The verification result outputting unit 64 outputs the suitability determination and degree of coincidence, which are results of verification performed in the comparison verification unit 63, to the display input device 3 to display the results. Here, the verification result outputting unit 64 also displays an image for verification which will be described below with reference to FIGS. 6(A) to 6(D). The images in FIGS. 6(A) to 6(D) are originally color images, but all have a fixed and higher density as compared to actual images for clarification of a difference on the patent drawings that show monochromatic images.

Figure 6:
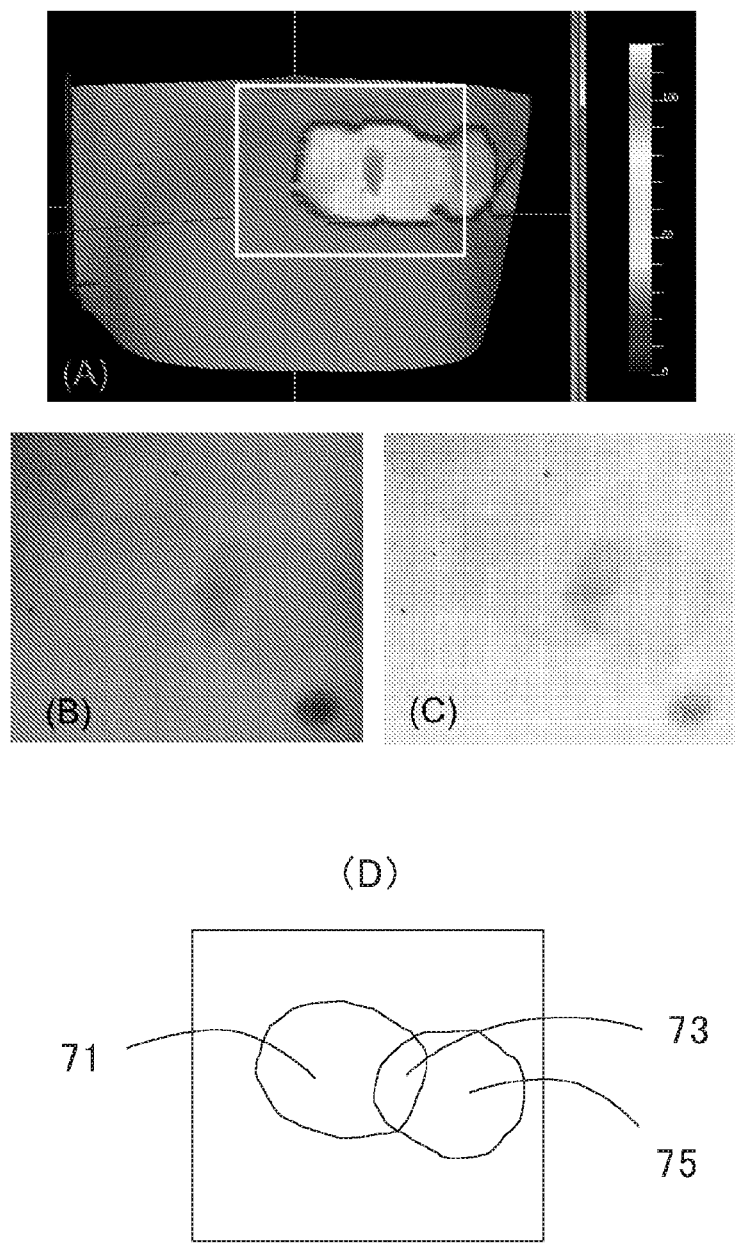
FIGS. 6(A) to 6(D) are explanatory views showing an image for verification of an exposure region.

FIGS. 6(A) to 6(D) are explanatory views showing an image for verification of an exposure region. FIG. 6(A) is a skin dose distribution image showing a distribution of skin doses calculated from a therapy plan. In the illustrated example, skin is exposed in two directions with a prescribed dose of 12.5 Gy (RBE) in one way, where the skin dose of 22 Gy (RBE) at a part with two-way exposures overlapping each other is set to 100%. FIG. 6(B) is a post-exposure skin image taken by performing photographing after exposure in the therapy plan shown in FIG. 6(A). In the post-exposure skin image, the rectangular white framed part in FIG. 6(A) is enlarged and shown. FIG. 6(C) is a hemoglobin pigment image obtained by pigmentarily resolving the post-exposure skin image. FIG. 6(D) is an explanatory view for explaining the exposure regions in FIGS. 6(A) to 6(C). In exposure in this example, a first exposure region 71, a second exposure region 75, and an overlapped exposure region 73 that is an overlapped part of the first exposure region 71 and the second exposure region 75 exist as illustrated. In this way, the images shown in FIGS. 6(A) to 6(C) are output by the verification result outputting unit 64, so that the skin dose distribution image in the therapy plan in FIG. 6(A) and the hemoglobin pigment image after therapy in FIG. 6(C) can be compared with each other to verify whether or not suitable exposure can be performed as planned.

The comparison verification unit 63 and the verification result outputting unit 64 may be configured such that a prediction skin image estimated from the skin dose distribution image (see FIG. 6(A)) in the therapy plan and the post-exposure skin image (hemoglobin pigment image in FIG. 6(C)) are displayed side by side on the display input device 3, and suitability is finally decided by physician's visual determination, input to the display input device 3, and then received. In this case, a configuration can be employed in which the result of verification in the comparison verification unit 63 is displayed on the display input device 3, and final determination is then left to a physician, or a configuration can be employed in which determination of suitability is totally left to a physician without performing comparison verification in the comparison verification unit 63.

By the above configuration and operation, a skin reaction to radiation exposure can be precisely predicted beforehand.

The prediction device 4 for skin change can clearly display change of skin after radiation exposure by means of a prediction skin image. Thus, the operator can visually and intelligibly know how much skin change occurs before radiation therapy is conducted.

The prediction device 4 for skin change can output a grade value that is more precise than before. Thus, for example when the grade value is grade 2, the operator can clearly know whether it is grade 2 close to grade 1 or it is grade 2 close to grade 3. Therefore, it can be made easy for the operator to optimally adjust the skin dose according to a predicted grade value before therapy.

The prediction device 4 for skin change can quantitatively output a precise grade value. Thus, the grade value can be used as a common scale in communication among physicians. The prediction device 4 for skin change can achieve standardization of the grade value as a scale showing skin change from radiation exposure.

Since the prediction device 4 for skin change displays the previous grade and the new grade side by side on the grade determination screen 50, a physician that is used to the previous grade can use the new grade without feeling uncomfortable. Particularly, by displaying the prediction value mark 53, the prediction device 4 for skin change can display the grade to a physician in an intrusively intelligible manner.

The prediction device 4 for skin change prepares a prediction skin image such that skin change from radiation exposure is change in relative amount with respect to the original skin image. Thus, the operator is not required to secure strictness regarding a photographing environment etc., and can easily and conveniently use the prediction device 4 for skin change.

The prediction device 4 for skin change does not require a special photographing environment such as polarized illumination, and it suffices that there is no unnatural non-uniformity in illumination (or natural light). Thus, skin images that are easily and conveniently taken in various environments using various cameras 2 can be used.

The verification device 6 can compare and verify a prediction skin image predicted by the prediction device 4 for skin change and a post-exposure skin image after skin is actually exposed to radiation. Accordingly, the operator can easily check whether or not radiation therapy has been conducted as planned. When there is a large error between the prediction skin image and the post-exposure skin image, the cause can be investigated to contribute to enhancement of prediction precision.

Figure 7:
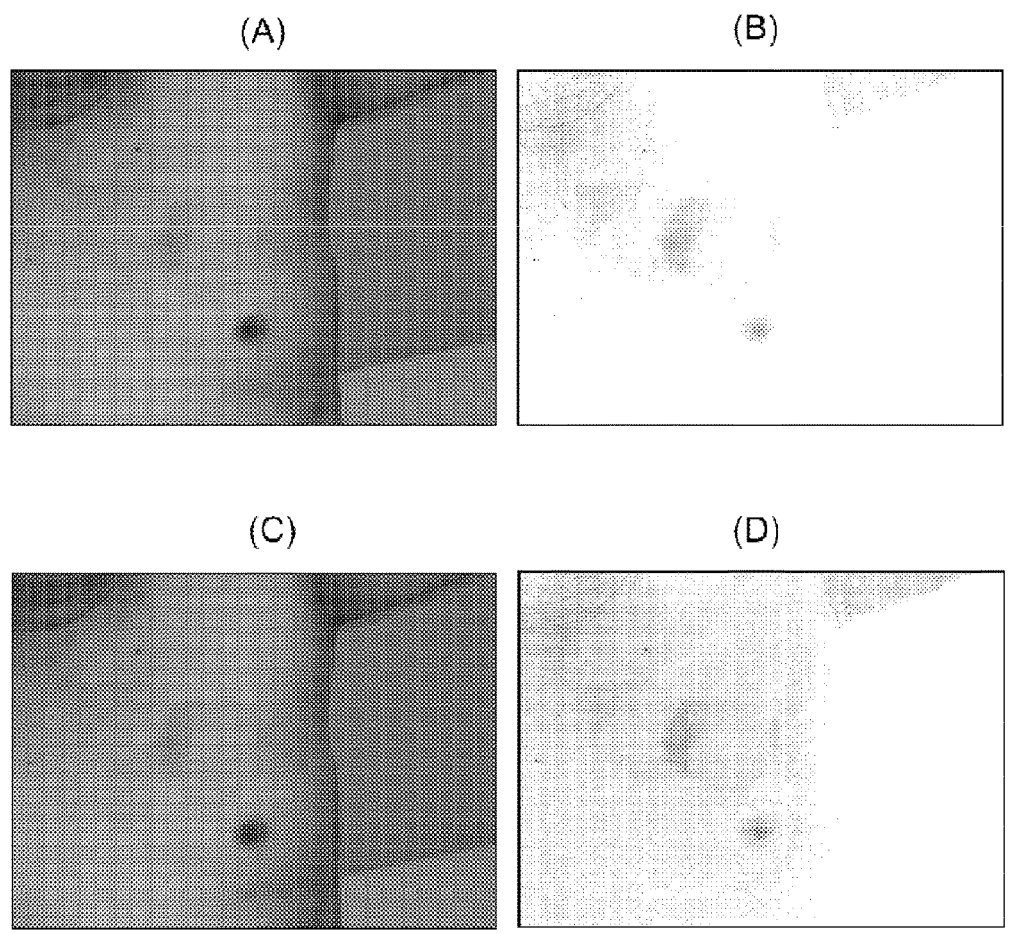
FIGS. 7(A) to 7(D) are explanatory views explaining a skin region sampling effect.

When a skin region is sampled by the skin region sampling unit 211, and calculation is then performed, the precision of pigment resolution can be improved as shown in the explanatory views of FIGS. 7(A) to 7(D). Specifically, FIG. 7(A) is a photographed image taken after exposure, and when a hemoglobin pigment image is obtained without sampling a skin region from the photographed image, a hemoglobin pigment image shown in FIG. 7(B) is obtained. On the other hand, when a skin region is sampled, and calculation is performed, a high-precision hemoglobin pigment image shown in FIG. 7(D) can be obtained from a photographed image shown in FIG. 7(C). The photographed images in FIG. 7(A) and FIG. 7(C) are the same. The images in FIGS. 7(A) to 7(D) are originally color images, but all have a fixed and higher density as compared to actual images for clarification of a difference on the patent drawings that show monochromatic images.

When an average of pixels in the RGB expression form is used for conversion between the RGB expression form and the color vector expression form, the conversion can be performed.

When the average is not an average over the whole image, but an average calculated from the RGB pixel values of only the skin region, the hemoglobin amount can be precisely estimated without being influenced by an illumination environment and a photographing environment. Specifically, influences of the background color and the color of clothing can be prevented, and anyone can easily use the technique under moderate photographing conditions. Even a photographed image which was taken in the past and which is not intended to be analyzed can be precisely analyzed to estimate the hemoglobin amount.

The present invention is not limited to the configuration of the embodiment described above, and many embodiments can be obtained.

For example, a hemoglobin vector and a melanin vector are used as color vectors in the embodiment described above, but the melanin component and other components may be got together to use the hemoglobin vector and others.

In this case, image changing may be performed for only the hemoglobin component, and therefore a prediction image for skin change from exposure to a skin dose can be appropriately prepared.

The present invention may be used not only for prediction of skin change from influences of radiation, but also for quantification of the condition of skin erythema caused by other factors, and prediction of skin erythema. In this case, the present invention can be used for prediction, and also made to contribute to correct grasping of the present state by quantification, and exchange of correct information among physicians.

INDUSTRIAL APPLICABILITY

The present invention can be used in industries in which influences of radiation exposure on skin are predicted, industries in which suitability of prediction is verified, and industries in which influences of skin erythema are quantified.

DESCRIPTION OF REFERENCE SIGNS

4: Prediction device for skin change
6: Verification device
11: Radiation information accepting unit
13: Amount-of-change deciding unit
14: Grade determining unit
21: Pre-exposure skin image acquiring unit
22: Expression form converting unit
23: Image changing unit
24: Expression form restoring unit
25: Prediction skin image outputting unit
61: Prediction skin image acquiring unit
62: Post-exposure skin image acquiring unit
63: Comparison verification unit
211, 311: Skin region sampling unit

The invention claimed is:

1. A prediction device for skin change from radiation exposure, the device comprising:
   a radiation information accepting unit that accepts input of radiation information regarding expected exposure to radiation;
   a skin image acquiring unit that acquires a skin image that captures skin of a living body;
   a change computing unit that computes the change of the skin due to exposure to the radiation determined by the radiation information and that obtains from the skin image a post-change prediction skin image, the change computing unit including:
      an expression form converting unit that converts the skin image from skin image color component data in an expression form associated with the original color component to skin image living body element component data in an expression form associated with a living body element component;
      an amount-of-change deciding unit that decides an amount of change in which a part of the skin image living body element component data is changed due to radiation exposure determined by the radiation information;
      a changing unit that changes the part of the skin image living body element component data according to the amount of change; and
      an expression form restoring unit that restores the post-change image to the expression form of the original color image; and
   an outputting unit that outputs the prediction skin image.

2. A prediction device for skin change from radiation exposure, the device comprising
   a radiation information accepting unit that accepts input of radiation information regarding expected exposure to radiation;
   a skin image acquiring unit that acquires a skin image that captures skin of a living body;
   a change computing unit that computes the change of the skin due to exposure to the radiation determined by the radiation information and that obtains from the skin image a post-change prediction skin image;
   an outputting unit that outputs the prediction skin image; and
   a grade value calculating unit that calculates a grade value in new grades more minute than the division units of the previous grades on the basis of the amount of change decided by the amount-of-change deciding unit.

3. A verification device, comprising:
   a prediction skin image acquiring unit that acquires the prediction skin image from a prediction device for skin change from radiation exposure, the prediction device for skin change from radiation exposure including:
      a radiation information accepting unit that accepts input of radiation information regarding expected exposure to radiation;
      a skin image acquiring unit that acquires a skin image that captures skin of a living body;
      a change computing unit that computes the change of the skin due to exposure to the radiation determined by the radiation information and that obtains from the skin image a post-change prediction skin image; and
      an outputting unit that outputs the prediction skin image;
   a post-exposure skin image acquiring unit that acquires a post-exposure skin image that captures skin after radiation exposure; and
   a verification unit that verifies whether or not radiation exposure is appropriately performed on the basis of the prediction skin image and the post-exposure skin image.

4. A non-transitory computer-readable medium that stores a prediction program for skin change from radiation exposure, when executed, the program causing a computer to function as:
   a radiation information accepting unit that accepts input of radiation information regarding expected exposure to radiation;
   a skin image acquiring unit that acquires a skin image that captures skin of a living body;
   a change computing unit that computes the change of the skin due to exposure to the radiation determined by the radiation information and that obtains from the skin image a post-change prediction skin image, the change computing unit including:
      an expression form converting unit that converts the skin image from skin image color component data in an expression form associated with the original color component to skin image living body element component data in an expression form associated with a living body element component;
      an amount-of-change deciding unit that decides an amount of change in which a part of the skin image living body element component data is changed due to radiation exposure determined by the radiation information;

a changing unit that changes the part of the skin image living body element component data according to the amount of change; and an expression form restoring unit that restores the post-change image to the expression form of the original color image; and an outputting unit that outputs the prediction skin image.

5. A non-transitory computer-readable medium that stores a verification program, when executed, the verification program causes a computer to function as:

a prediction skin image acquiring unit that acquires the prediction skin image from the prediction program for skin change from radiation exposure;

a radiation information accepting unit that accepts input of radiation information regarding expected exposure to radiation;

a skin image acquiring unit that acquires a skin image that captures skin of a living body;

a change computing unit that computes the change of the skin due to exposure to the radiation determined by the radiation information and that obtains from the skin image a post-change prediction skin image; and an outputting unit that outputs the prediction skin image;

a post-exposure skin image acquiring unit that acquires a post-exposure skin image that captures skin after radiation exposure; and a verification unit that verifies whether or not radiation exposure is appropriately performed on the basis of the prediction skin image and the post-exposure skin image.

6. A method for predicting skin change, the method comprising:

accepting factor information regarding a factor of change of skin of a living body using a factor information accepting unit;

acquiring a skin image that captures the skin of the living body using a skin image acquiring unit;

obtaining a post-change prediction skin image from the skin image by computing change of the skin due to occurrence of a factor, which is determined by the factor information, using a change computing unit, the change computing unit including:

an expression form converting unit that converts the skin image from skin image color component data in an expression form associated with the original color component to skin image living body element component data in an expression form associated with a living body element component;

an amount-of-change deciding unit that decides an amount of change in which a part of the skin image living body element component data is changed due to radiation exposure determined by the radiation information;

a changing unit that changes the part of the skin image living body element component data according to the amount of change; and an expression form restoring unit that restores the post-change image to the expression form of the original color image; and outputting the prediction skin image using an outputting unit.

* * * * *